United States Patent [19]

Nilsson et al.

[11] Patent Number: 5,691,350
[45] Date of Patent: Nov. 25, 1997

[54] USE OF LINOMIDE FOR TREATMENT OF RETROVIRUS INFECTIONS SPECIFICALLY HIV INFECTIONS

[75] Inventors: Bo Nilsson, Helsingborg; Terje Kalland, Löddeköpinge, both of Sweden

[73] Assignee: Kabi Pharmacia AB, Helsingborg, Sweden

[21] Appl. No.: 462,050

[22] Filed: Jun. 5, 1995

Related U.S. Application Data

[63] Continuation of Ser. No. 191,438, Feb. 3, 1994, abandoned, which is a continuation of Ser. No. 920,311, filed as PCT/SE91/00136, Feb. 21, 1991 published as WO91/12804, Sep. 5, 1991, abandoned.

[30] Foreign Application Priority Data

Feb. 22, 1990 [SE] Sweden .................................... 9000624

[51] Int. Cl.$^6$ ................................................ A61K 31/47
[52] U.S. Cl. ............................................................ 514/312
[58] Field of Search ............................................... 514/312

[56] References Cited

U.S. PATENT DOCUMENTS 4,547,511 10/1985 Eriksoo .................................... 514/312

OTHER PUBLICATIONS

Larsson et al., *Int. J. Immunopharmacol.*, 9:425 (1987).
Carlsten H. et al., *APMIS*, 97:728 (1989).
Kalland et al., *J. Immunol.*, 134:3956 (1985).
Kalland et al., *J. Immunol.*, 144:4472–6 (1990).
Namikawa et al., *Science*, 242:1684–6 (1988).
Putkonen et al, *J. AIDS Res.*, 2:359–365 (1989).
Thorstensson, et al., *J. AIDS*, "A capture immunoassay for detection of HIV–2/SIV Antigen" in press 1989.
Kalland, STN International, File CA, Chemical Abstracts, vol. 103, No. 15, Oct. 14, 1985.
Werner, *Drugs of Today*, vol. 26, No. 4, 1990, pp. 269–277.
St. Georgieu Vassil, *Trends in Pharmacological Sciences*, vol. 9, No. 12, 1988, p. 446–451.
Montagnier, *Ann. Virol. Inst. Pasteur 135 E*, pp. 119–134 (1984).
Guyader, *Nature 326*, p. 662 (1987).
Koff and Hoth, *Science 241*, pp. 426–432 (1988).
Gottlieb, "Immunotherapy of the acquired immune deficiency syndrome", In: Gallin JI, Fauci AS eds. New York: Raven Press, 5:149–70 (1985).
Lotze, In: De Vita VT, et al., eds., *AIDS Etiology, Diagnosis Treatment and Prevention*, New York, Lippincott JB Company, pp. 235–263 (1985).
Popovic et al., *Science 224*, pp. 497–500 (1984).
Ilbaeck et al., File CA, Chemical Abstracts, vol. 110, 205297p, 1989.
Ilbaeck et al., File CA, Chemical Abstracts, vol. 110, 88192n, 1989.
Morahan et al., File CA, Chemical Abstracts, vol. 109, 122145r, 1988.

Morahan et al., "Immunopharmacology of infectious disease: Vaccine Adjuvants and Modulators of Non–Specific Resistance", pp. 313–324, 1987.
Vella et al., "Survial of Zidovudine–Treated Patients with Aids Compared with That of Contemporary Untreated Patients", *JAMA*, Mar., 1992, vol. 267, No. 9, pp. 1232–1236.
Montagnier, et al., *Ann. Virol. (Inst. Pasteur) 135 E*, 119–134, 1984.
Davis, *Microbiology*, Seconc Edition, Chapter 55, pp. 1280–1287.
McKinlay, *Scand J. Infect Dis* —Suppl. vol. 88, pp. 109–115, 1993.
St. Georgieu, *Trends in Pharmacological Sciences*, vol. 9, No. 12, 1988, pp. 446–451.
Kalland et al., *J. Immunol.* 134:3956, 1985.
Carlsten H. et al., *APMIS*, 97:728, 1989.
Koff and Hoth, *Science*, vol. 241, pp. 426–432, 1988.
Gallo et al., *Science*, vol. 224, pp. 500–503, 1984.
Popovic et al., *Science*, vol. 224, pp. 497–500, 1984.
Guyader, *Nature*, vol. 326, p. 662, 1987.
Lotze, In: De Vita VT, et al., eds., *AIDS Etiology, Diagnosis, Treatment and Prevention*, New York, Lippincott JB Company, pp. 235–263, 1985.
Larsson et al., *Int. J. Immunopharmacol.*, 9:425, 1987.
Kalland et al., *J. Immunol.*, 144:4472–6, 1990.
Namikawa et al., *Science*, 242:1684–6, 1988.
Thorstensoon, et al., *Journal of Acquired Immunodeficiency Syndrome*, "A capture immunoassay for detection of HIV–2/SIV Antigen" 4: 374–379, 1991.
Putkonen, *Journal of Acquired Immune Deficiency Syndrome*, 2:359–365, 1989.
Putkonen, "Monkey Models for Evaluation of HIV Vaccines", Doctoral Thesis, Dept. of Immunology, National Bacteriological Laboratory, Department of Virology, Karolinska Institute, 1991.
Cohen, *Science*, vol. 260, p. 157, Apr., 1993.
Ruedy et al., *AIDS*, 7:189–196, 1993 (MEDLINE Abstracts).
Van Rompay et al, *Antimicrobial Agents and Chemotherapy*, 36:2381–2386, 1992. (MEDLINE Abstracts).
McClure, *Annuals of the N.Y. Academy of Science*, 616:287–298, 199 (MEDLINE Abstracts) 1989.
Skowron, *Hosp–Pract–Off–Ed*, Suppl 2: 5–13, Aug., 1992 (MEDLINE Abstracts).
Ilbäck, *The Journal of Immunology*, vol. 142, pp. 3225–3228, No. 9, May, 1989.
Ilbäck, *Antiviral Research*, 10, pp. 129–140, 1988.
Bottiger, et al., *AIDS Research in Human Retroviruses*, vol. 8, No. 7, pp. 1235–1238, 1992.

(List continued on next page.)

*Primary Examiner*—Russell Travers
*Attorney, Agent, or Firm*—Pravel, Hewitt, Kimball & Krieger

[57] ABSTRACT

The present invention concerns the use of Linomide® or a pharmaceutically acceptable salt thereof for the manufacture of a medicament for the treatment of retrovirus infections. Specifically the invention concerns the treatment of HIV infections.

11 Claims, 5 Drawing Sheets

OTHER PUBLICATIONS

Lundgren et al., *Antiviral Chemistry and Chemotherapy*, 5:299–306, 1990.

Putkonen, et al., *Journal of Acquired Immune Deficiency Syndromes*, "Experimental Infection of Cynomolgus Monkeys", 2:366–373, 1989.

Putkonen, et al., *Aids Research and Human Retroviruses*, "Vaccine Protection Against HIV-2 Infection in Cynomolgus Monkeys", vol. 7, No. 3, 1991.

Feichtinger, et al., *American Journal of Pathology*, vol. 137, No. 6, pp. 1311–1315, 1990.

Putkonen, et al, *AIDS*, vol. 4, No. 8, pp. 784–789.

Morahan, *Prog. Leukoyte Biology*, 6:313–324, 1987.

Ilbaeck et al 110 CA: 205297p 1989 (1989).

Ilbaeck et al 110 CA 88192n 1989 (1988).

Morahan et al 109 CA:122145r 1987.

Figure 1A
Low dose Linomide 0.3 mg/kg x2

- L1
- L2
- L3

Weight (g) vs Days postinoculation with SIVsm

Figure 1B
High dose Linomide 3 mg / kg x2

- L4
- L5
- L6

Weigth (g) vs Days postinoculation with SIVsm

Figure 1C
Control animals

- L7
- L8
- L9

Weigth (g) vs Days postinoculation with SIVsm

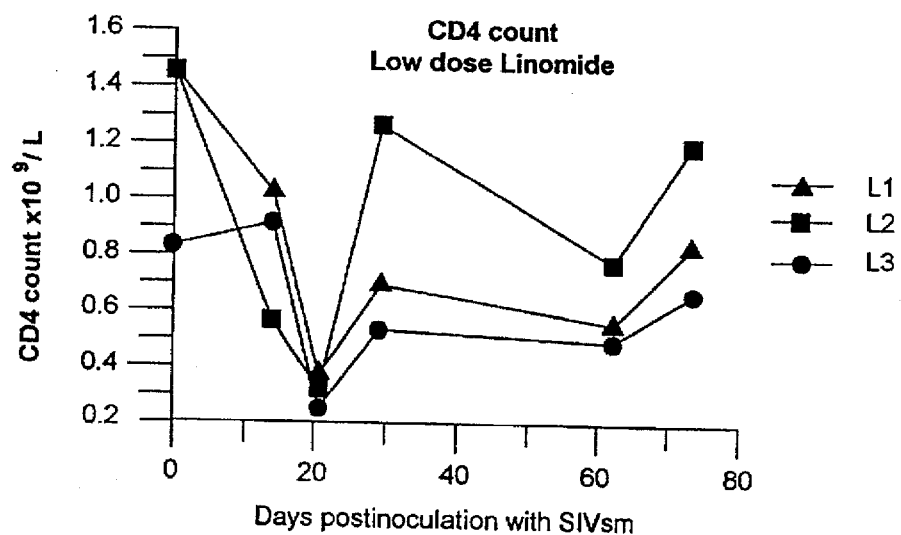
Figure 2A — CD4 count Low dose Linomide
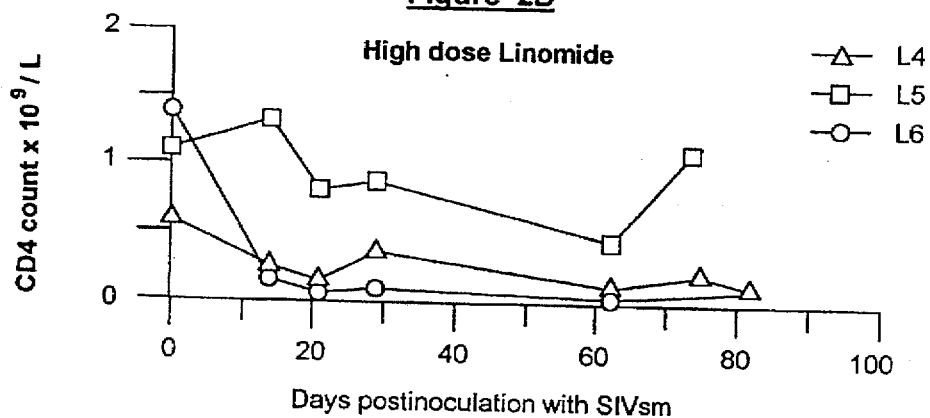
Figure 2B — High dose Linomide
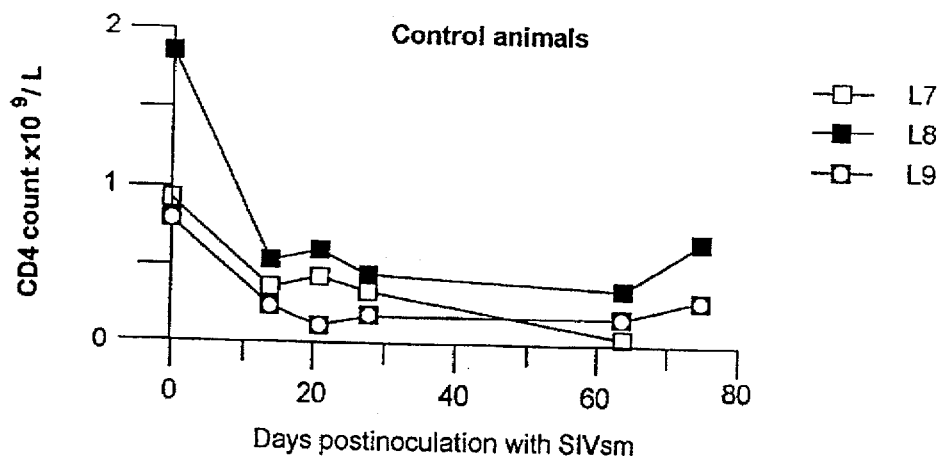
Figure 2C — Control animals

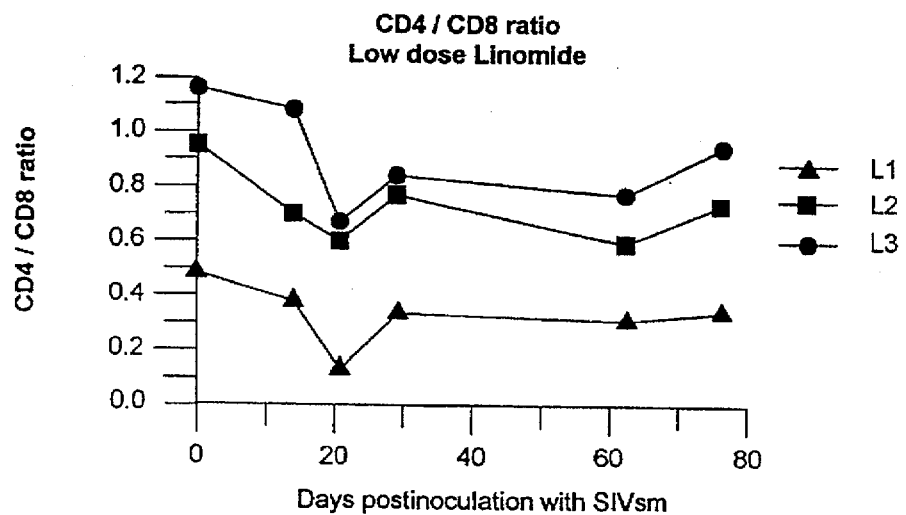
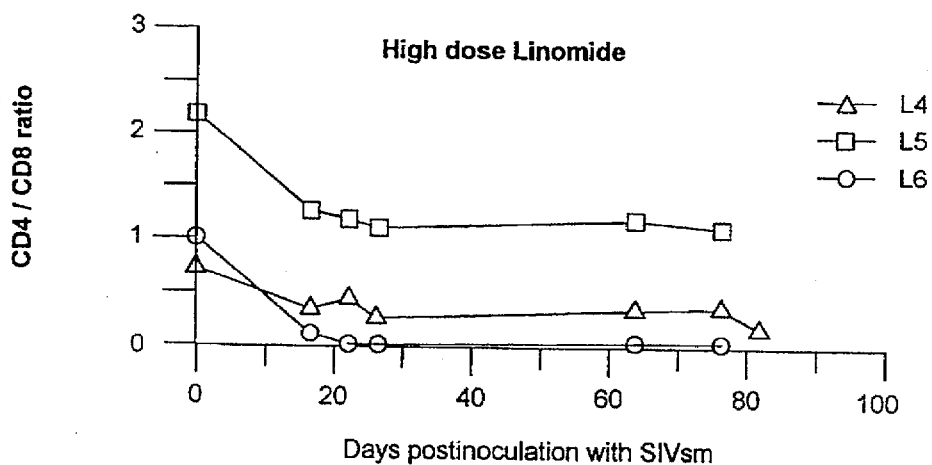
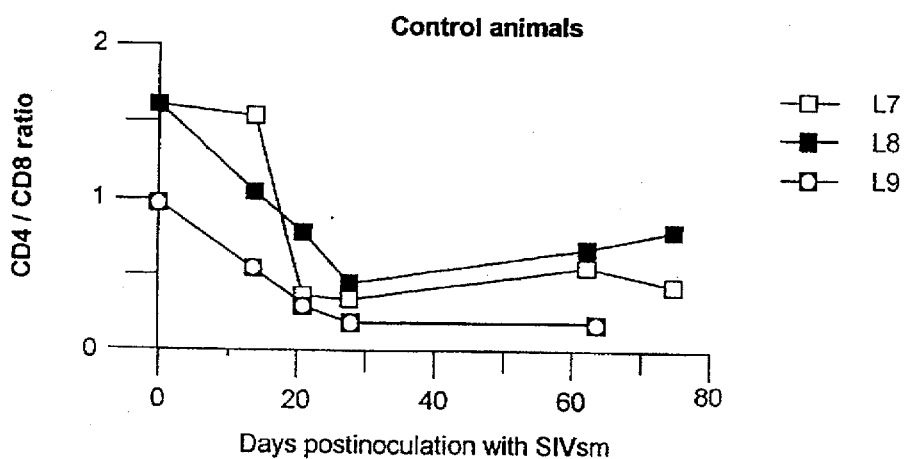

Figure 5

Table 1: Results of virus isolation.

| | Monkeys treated with Linomide | | | | | | Control animals | | |
| --- | --- | --- | --- | --- | --- | --- | --- | --- | --- |
| | 0.3 mg / kg x 2 | | | 0.3 mg / kg x 2 | | | NaCl | | |
| Day | L1 | L2 | L3 | L4 | L5 | L6 | L7 | L8 | L9 |
| 0 | - | - | - | - | - | - | - | - | - |
| 14* | + | + | + | + | + | + | + | + | + |
| 28 | + | + | + | + | + | + | + | + | + |
| 62 | + | + | + | + | + | + | + | + | + |

\* Presence of viral antigen in serum was demonstrated in all nine monkeys 14 days after challenge

USE OF LINOMIDE FOR TREATMENT OF RETROVIRUS INFECTIONS SPECIFICALLY HIV INFECTIONS

This is a continuation of application Ser. No. 08/191,438, filed on Feb. 3, 1994 now abandoned which is a continuation of Ser. No. 07/920,311, filed on Aug. 12, 1992 now abandoned and PCT/SE91/00136 filed on Feb. 21, 1991 now WO/91/12804, Sep. 5, 1991.

This invention relates to the use of N-phenyl-N-methyl-1,2-hydro-4-hydroxy-1-methyl-2-oxo-quinoline-3-carboxamide or a pharmaceutically acceptable derivative thereof for the manufacture of a medicament having potential use for the treatment of retrovirus infections, specifically HIV infections, and of patients suffering from acquired immune deficiency syndrome (AIDS) and AIDS related complex (ARC).

BACKGROUND

Acquired immune deficiency syndrome (AIDS) has emerged as a mortal human disease of increasing global importance. As there is no effective therapy known for the treatment of AIDS, new methods of therapy are urgently needed, and great efforts are being made to develop drugs and vaccines to combat AIDS.

The AIDS virus, first identified in 1983, has been described. by several names. It is the third known T-lymphocyte virus (HTLV-III) and has the capacity to replicate within cells of the immune system and thereby lead to a profound destruction of T4 T-cells (or CD4 cells). See e.g. Gallo et al., Science 224, 500–503 (1984), and Popovic et al., Ibid., 497–500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [Ann. Virol. Inst. Pasteur 135 E, 119–134 (1984)], while HIV-2 was more recently isolated by Montagnier and his coworkers in 1986 [Nature 326, 662 (1987)]. As used herein, HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, e.g. Koff and Hoth, Science 241, 426–432 (1988).

The first drug to be approved by the US Food and Drug Administration (FDA) for treatment of AIDS was zidovudine, better known under its former name azidothmidine (AZT). Chemically, this drug is 3'-azido-3-deoxythymidine. This drug was originally selected as a potential weapon against AIDS because it was shown to inhibit replication of the virus in vitro. A serious drawback of AZT, however, is its toxic side-effects. In addition to AZT other antiviral agents such as Anasamycin, Ribovirin, Dideoxycytidine and Foscarnet have been developed. So far, however, these agents do not seem to be more advantageous than AZT. Also immunostimulating or immunoadoptive treatments with IFNs or IL2, thymic hormones and factors, transfer factor, and treatments with so called immunostimulating drugs, e.g. isoprinosine, azimexon, tuftsin, bestatin, cimetidine, thymic transplants and HLA matched lymphocyte transfusions or siblings or identical twin bone marrow transplants have been tested but seem to have failed, as underlined in two recent reviews (Gottlieb M. S. et al, Immunotherapy of the acquired immune deficiency syndrome, In: Gallin J. I., Fauci A. S., eds. Advances in host defense mechanisms. New York: Raven Press, 1985;5:149–70, and Lotze M. T. Treatment of immunologic disorders in AIDS. In De Vita V. T., Hellman S., Rosenberg S. A. eds. AIDS etiology, diagnosis, treatment, and prevention. New York: Lippincott J. B. company, 1985:235–63).

SUMMARY OF THE INVENTION

According to the present invention it has now surprisingly been shown that N-phenyl-N-methyl-1,2-dihydro-4-hydroxy-1-methyl-2-oxo-quinoline-3-carboxamide has properties that might be useful for the treatment of retrovirus infections, such as HIV infections on mammals including humans, and of patients suffering from AIDS and ARC. N-phenyl-N-methyl-1,2-dihydro-4-hydroxy-1-methyl-2-oxo-quinoline-3-carboxamide is also known under the name Linomide® and the generic name roquinimex. The invention also concerns the use of Linomide® or a pharmaceutically acceptable salt thereof such as the Na or Ca salt for the manufacture of a drug for the treatment of retrovirus infections, especially HIV infections, and of patients suffering from AIDS and AIDS related complex. Linomide® was first described in the U.S. Pat. No. 4,547,511 as an immunostimulating agent.

The scientific experimentation with Linomide® has shown that Linomide® has multiple immunological activities. It has thus been found that Linomide® increases the proliferative response to T and B cell mitogens [Larsson, E. L., Joiki, A. L. and Stålhandske, T.: Mechanism of action of the new immunomodulator L. S. 2616, Int. J. Immunopharmacol. 9:425, 1987], enhances antibody production [Carlsten, H., Tarkowski, A., and Nilsson, L.-Å: The effect of immunomodulating treatment on cutaneous delayed hypersensitivity in MRL (1pr/1pr) mice, APMIS 97:728, 1989] and augments NK cell activity [Kalland, T., Alm, G., and Stålhandske, T.: Augmentation of mouse natural killer cell activity by L. S. 2616, a new immunomodulator, J. Immunol. 134:3956, 1985], [Kalland, T.: Regulation of NK progenitors: Studies with a novel immunomodulator with distinct effects at the precursor level, J. Immunol. 144:4472–6, 1990,].

In view of the fact that Linomide® has been shown to stimulate the T lymphocytes and increase the production of IL-2 it could not be expected that Linomide® should show effect on retrovirus infections as attempts to treat HIV infected patients with the T cell growth hormone IL-2 accelerated the disease. No doubt, it can be said that stimulation of T lymphocytes in patients with HIV-infections may be a two-edged sword. T helper cells are pivotal in the generation of an immune response, but also the reservoir for the replicating HIV-virus. Also, in view of the fact that the previous experiments with immunostimulating agents have not been successful it is interesting to see the promising results of Linomide®.

Linomide® has the following structural formula:

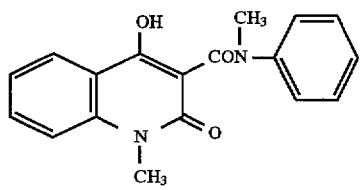

Linomide® may be used as such or as a salt of pharmaceutically acceptable cation. Furthermore, Linomide® can be used in combination with other anti-AIDS agents.

A conceivable Linomide® dosage range in the treatment of AIDS would be from about 0.1 to about 100 mg a day or possibly higher depending upon the specific condition to be treated, the age and weight of the specific patient, and the specific patient's response to the medication. The exact individual dosage, as well as the daily dosage, will be determined according to standard medical principles under the direction of a physician.

Formulations that could be used according to the present invention are disclosed in U.S. Pat. No. 4,547,511 col. 11, which is hereby incorporated by reference.

As stated above Linomide® is a potent stimulator of T lymphocytes and augments the production of IL-2. The immunpharmacological profile, however, is dominated by a profound increase in natural killer (NK) cell activity with less effects on T cell activity in vivo [Kalland, T.: Effects of the immunomodulator LS 2616 on growth and metastasis of the murine B16-F10 melanoma, Cancer Res. 46:3018, 1986]. In particular, the frequency of CD4 expressing cells is not increased during treatment of mice with Linomide® (Example 2) This finding in combination with promising results on retrovirus infected monkeys makes Linomide® potentially useful in treatment of retrovirus including HIV-infections, AIDS and ARC in spite of potential hazards related to the T cell stimulating properties of Linomide®.

The invention is further illustrated by the following examples.

BRIEF DESCRIPTION OF THE DRAWINGS

FIGS. 1(A–C) shows the body weight of control animals and experimental animals treated with a low and high dose of Linomide®;

FIGS. 2(A–C) shows the CD4 count of control animals and experimental animals treated with a low and high dose of Linomide®;

FIGS. 4(A–C) shows the CD4/CD8 ratio of control animals and experimental animals treated with a low and high dose of Linomide®; and FIG. 5 shows the results of virus isolation.

EXAMPLE 1

Effect of Linomide® on NK activity

Figure 3A:
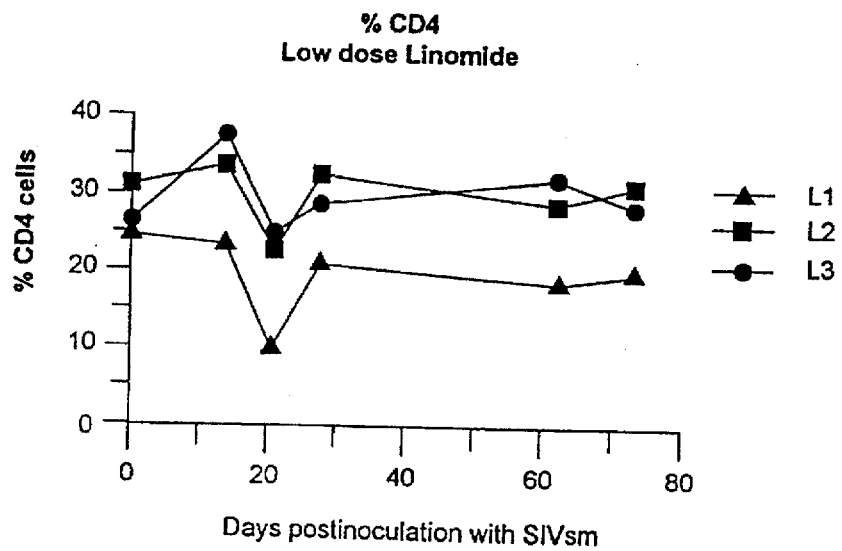
FIGS. 3(A–C) shows the % CD4 cells of control animals and experimental animals treated with a low and high dose of Linomide®.

| Treatment | % CYTOTOXICITY | | |
|---|---|---|---|
| | 100:1* | 50:1* | 25:1* |
| Control | 18 ± 4 | 12 ± 2 | 8 ± 2 |
| Linomide ® | 29 ± 5 | 20 ± 4 | 14 ± 4 |

*Effector cell: Target cell ratio

Linomide® (160 mg/kg/day) was given in the drinking water for four days and spleen NK activity against YAC-1 cells determined by a conventional $^{51}$Cr-release assay as described [Kalland, T., Alm, G., and Stålhandske, T.: Augmentation of mouse natural killer cell activity by L. S. 2616, a new immunomodulator, d. Immunol, 134:3956, 1985]. The result from one experiment with 3 C5781/6 mice per treatment group is shown and demonstrate that Linomide® significantly enhances NK activity.

EXAMPLE 2

Effect of treatment with Linomide® on spleen T lymphocyte subpopulations:

| Treatment | % Fluorescent cells | | |
|---|---|---|---|
| | Thy 1.2 | CD4 | CD8 |
| Control | 44 ± 4 | 31 ± 2 | 11 ± 2 |
| Linomide | 42 ± 5 | 28 ± 2 | 10 ± 3 |

C5781/6 mice were given Linomide® (160 mg/kg/day) in the drinking water for 4 days. Control animals were given ordinary drinking water. Spleen cells were prepared as described [Kalland, T.; Alm, G., and Stålhandske, T.: Augmentation of mouse natural killer cell activity by LS 2616, a new immunomodulator, J. Immunol. 134:3956, 1985] and examined for the expression of cell surface markers by direct immunofluorescence. The following FITC-labeled monoclonal antibodies were used: HO-134 (Thy 1.2), GK 1.5 (CD4) and 19.178c (CD8) [for reference to antibodies see Kalland, T.: Regulation of NK progenitors: Studies with a novel immunmodulator with distinct effects at the precursor level, J. Immunol., 144:4472–6, 1990]. The number of positive cells was determined by counting 400 cells in an epifluoroscence equipped Leitz microscope, Values represent mean±SD of three mice. The data suggest that Linomide® do not significantly altler the distribution of T lymphocyte subpopulations.

The results which were obtained with Linomide® and are presented in Examples 1 and 2 show that Linomide® is of potential use in the treatment of HIV-infections.

EXAMPLE 3

The following experiments with SIV virus support the above in vitro results.

Background of the test model

Since the HIV-viruses do not infect the most commonly used experimental animals such as rats and mice, alternative models have to be utilized to examine the effect of potential drugs in vivo. Two principally different approaches can be taken. Scid mice have successfully been reconstituted with human haematopoietic cells and found to be able to carry HIV-virus infected lymphocytes (Namikawa, R., Kaneshima, H., Lieberman, M., Weissman, I. L., McCune, J. M.: Infection of the SCID-hu mouse by HIV-1. Science 242:1684–6, 1988). However, the relevance of this model is somewhat questionable, in particular for the investigation of drugs not directly interfering with virus replication but merely acting on host cells. Various species of monkeys have been tested as vehicles for different HIV or SIV viruses. SIV infection of cynomolgus monkeys results in an infection with many similarities to that of AIDS in the human (Putkonen, P., Warstedt, K., Thorstensson, R., Benthin, R., Albert, J., Lundgren, B., Öberg, B., Norby, E., Biberfeld, G., Experimental infection of cynomolgus monkeys (Macaca Fascicularis). with simian immunodeficiency virus (SIVsm). J. AIDS Res. 2:359–365; 1989). Virus can be isolated from lymphoid cells and lymph nodes at particular stages of infection, and antibodies to SIV is readily detectable. Moreover, a profound decrease in the absolute and relative number of $CD4^+$ T cells is a consistently observed. The animals develop clinical disease characterized by enlarged lymph nodes, opportunistic infections, weight loss and wasting syndrome. This model is probably one of the most relevant for in vivo testing of vaccines and drugs designed to treat HIV-infections in humans.

Materials and methods

Animals

Nine cynomolgus monkeys (Macaca Fascicularis) were used in this study. The mean body mass was 2600 g and the range was 2260 to 2930 g. The monkeys were housed in single cages in a biosafety level three facility. Before use, the animals were controlled for clinical health by physical examination and were confirmed to be free of SIV antibodies by ELISA [Putkonen, P., Warstedt, K., Thorstensson, R., Benthin, R., Albert, J., Lundgren, B., Öberg, B., Norrby, E., Biberfeld, G.: Experimental infection of cynomolgus monkeys (Macaca Fascicularis) with simian immunodeficiency virus (SIVsm), J. AIDS 1989:2, 359–365]. The absence of pre-existing retrovirus was further investigated by cocultivating monkey PBMC (=peripheral blood mononuclear cells) with human PHA-stimulated PBMC and testing of culture supernatants for reverse transcriptase activity.

Virus source

As in previous studies [Putkonen, P., Warstedt, K., Thorstensson, R., Benthin, R., Albert, J., Lundgren, B., Öberg, B., Norrby, E., Biberfeld, G.: Experimental infection of cynomolgus monkeys (Macaca Fascicularis) with simian immunodeficiency virus (SIVsm), J. AIDS 1989:2, 359–365] we used a SIV strain isolated from a naturally infected sooty mangabey monkey (SIVsm). A stock of this virus was previously titred in vivo in monkeys.

Experimental design

Intraperitoneal treatment with Linomide® or NaCl started four days before challenge with live virus and subsequently every day (not during weekends) subcutaneosly during the time of follow-up. The follow-up is 75 days after live virus challenge.

Monkeys L1–3 were treated with a low dose Linomide® 0.3 mg/kg bw×2 Monkeys L4–6 were treated with a high dose Linomide® 3 mg/kg bw×2 Monkeys L7–9 were given sodium chloride×2

All monkeys were challenged with 10–100 animal $ID_{50}$ of live SIVsm. Animals were sacrificed when they became modribund.

Virus isolation and viral antigen detection

Virus isolations were performed as previously described [Putkonen, P., Warstedt, K., Thorstensson, R., Benthin, R., Albert, J., Lundgren, B., Öberg, B., Norrby, E., Biberfeld, G.: Experimental infection of cynomolgus monkeys (Macaca Fascicularis with simian immunodeficiency virus (SIVsm), J. AIDS 1989:2, 359–365] with one important improvement. The culture supernatants were screened by a sensitive HIV-2/SIV antigen assay [Thorstensson, R., Walther, L., Putkonen, P. Albert, J., Biberfeld, G: A capture immunoassay for detection of HIV-2/SIV antigen, J. AIDS in press]. Presence of viral antigen in serum was demonstrated as previously. described [Thorstensson, R., Walther, L., Putkonen, P., Albert, J., Biberfeld, G: A capture immunoassay for detection of HIV-2/SIV antigen, J. AIDS in press].

Serological assays

Not tested so far.

Lymphocyte surface markers

T-lymphocyte subsets in peripheral blood were determined by immunofluorescence as previously described [Putkonen, P., Warstedt, K., Thorstensson, R., Benthin, R., Albert, J., Lundgren, B., Öberg, B., Norrby, E., Biberfeld, G.: Experimental infection of cynomolgus monkeys (Macaca Fascicularis with simian immunodeficiency virus (SIVsm), J. AIDS 1989:2, 359–365]. Peripheral blood samples were incubated with FITC-cojugated anti-CD4 (OKT4, Ortho) and anti-CD8 (Leu2, Becton Dickinson). The samples were analyzed in a Spectrum III flow cytometer (Ortho Diagnostics).

Results

All nine monkeys became infected as determined by virus isolation (Table 1). Virus was isolated from all animals on day 14, 28 and 62. Presence of vital antigen in serum was demonstrated 14 days after challenge in all nine monkeys.

Monkeys L4, L6 and L9 were sacrificed 70–82 days after challenge because of severe weight loss and rapid decrease of CD4+ cells (AIDS-like disease). Currently, monkey L7 also is in a bad clinical condition.

Enlargement of peripheral lymph nodes were observed in monkeys L3 and L7.

Monkeys L1–3 have remained clinically healthy.

Weight curves, CD4 count, % CD+ cells and CD4/8 ratio are shown in FIGS. 1–4.

The body weight of the animals is shown in FIG. 1. Only a slight weight reduction is seen in monkeys L1–3 treated with 0.6 mg/kg/day Linomide®. In contrast, one monkey in each of the control group (L9) and one in the high dose Linomide® group showed a dramatic reduction in body weight.

Figure 3B:
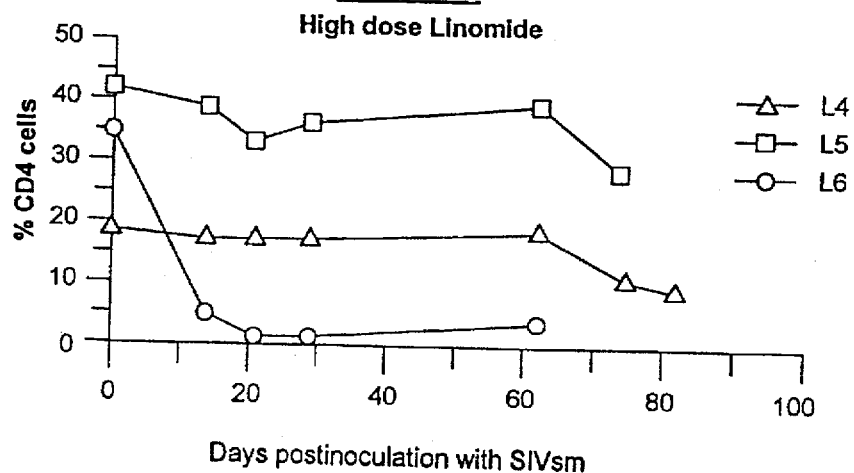
Figure 3C:
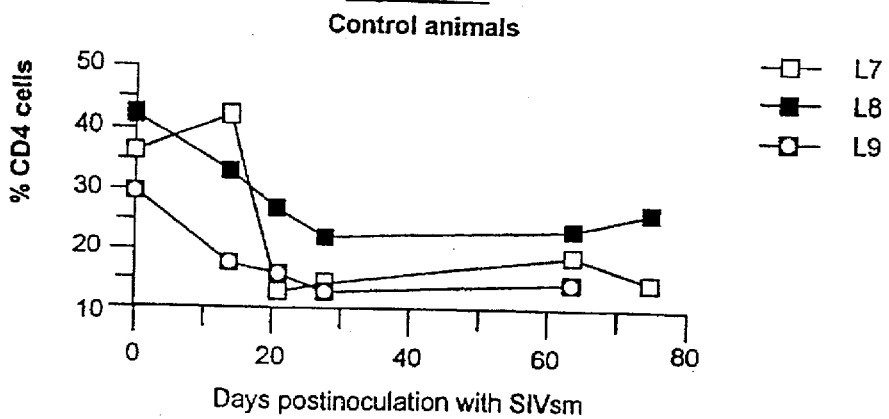

The absolute number and percentage of $CD4^+$ T lymphocytes in peripheral blood was followed with regular intervals during the experiment. The number of CD4+ lymphocytes was severly reduced in the control group at day 75 (0.33× $10^9/l$, 28% of start value) but only slightly reduced in the low dose Linomide® treated group (0.92×$10^9/l$, 70% of start value)(FIG. 2). Similarly, the percentage of $CD4^+$ cells in peripheral blood was reduced in control monkeys, but essentially unaltered in monkeys treated with low dose Linomide® (FIG. 3). The high dose Linomide® treatment did not significantly alter the number or frequency of CD4 cells in infected monkeys. In a qualitative virus isolation assay, virus could be isolated from all monkeys 14 days after challenge and vital antigens was demonstrated up to 62, the latest time included for this test (Table 1).

The half life of Linomide® differs markedly between species. It is two hours in mice, six hours in cynomolgus monkeys, 24 hours in rats and about 48 hours in humans. The lower dose of Linomide® in the present investigation (0.3 mg/kg×2daily) was based on extrapolations of data on half-life and optimal immunomodulatory activity in mice, rats and humans. Although the dose-response curve of Linomide® in common with many other biological response modifiers have been shown to be bell-shaped, a supra optimal dose (3 mg/kg×2 daily) was also included to examine possible direct effects of Linomide® on viral replication.

We claim:

1. A method for treating a mammal infected with a retrovirus which comprises administering to a mammal in need of such treatment a therapeutically effective amount of N-phenyl-N-methyl-1,2-dihydro-4-hydroxy-1-methyl-2-oxo-quinoline-3-carboxamide or a pharmaceutically acceptable salt thereof.

2. A method for treating a patient infected with an HIV virus comprising administering to a patient in need of such treatment a therapeutically effective amount of N-phenyl-N-methyl-1,2-dihydro-4-hydroxy-1-methyl-2-oxo-quinoline-3-carboxamide or a pharmaceutically acceptable salt thereof.

3. The method according to claim 2 wherein N-phenyl-N-methyl-1,2-dihydro-4-hydroxy-1-methyl-2-oxo-quinoline-3-carboxamide is administered in combination with another anti-AIDS agent.

4. The method according to claim 1 where the administration is oral.

5. The method according to claim 1 where the administration is parenteral.

6. The method according to claim 1, wherein said mammal is a human.

7. The method according to claim 1, wherein said retrovirus is an HIV virus.

8. A method for treating a patient suffering from AIDS or AIDS related complex which comprises administering to a patient in need of such treatment a therapeutically effective amount of N-phenyl-N-methyl-1,2-dihydro-4-hydroxy-1-methyl-2-oxo-quinoline-3-carboxamide or a pharmaceutically acceptable salt thereof.

9. The method of claim 8 wherein N-phenyl-N-methyl-1,2-dihydro-4-hydroxy-1-methyl-2-oxo-quinoline-3-carboxamide is administered in combination with another anti-AIDS agent.

10. The method of claim 8 wherein the administration is oral.

11. The method of claim 8 wherein the administration is parenteral.

* * * * *